United States Patent [19]

Lane

[11] Patent Number: 5,503,825
[45] Date of Patent: Apr. 2, 1996

[54] LIP BALM COMPOSITION

[76] Inventor: Barry Lane, Macon Hwy., P.O. Box 68, Bolingbroke, Ga. 31004-0068

[21] Appl. No.: 179,201

[22] Filed: Jan. 10, 1994

[51] Int. Cl.$^6$ .................................................. A61K 7/025
[52] U.S. Cl. ........................ 424/64; 424/195.1; 424/401; 424/680
[58] Field of Search .................. 424/64, 195.1, 424/680, 401; 514/969

[56] References Cited

U.S. PATENT DOCUMENTS

| 4,500,510 | 2/1985 | Goldstein | 424/80 |
| 5,215,760 | 6/1993 | Kavoussi et al. | 424/680 |
| 5,271,943 | 12/1993 | Bogart et al. | 424/484 |
| 5,288,492 | 2/1994 | Morris | 424/678 |

OTHER PUBLICATIONS

Facts and Comparisons, Kastrup et al. 1985, J. B. Lippincott Co., p. 506.

*Primary Examiner*—Thurman K. Page
*Assistant Examiner*—James M. Spear
*Attorney, Agent, or Firm*—Dominik & Stein

[57] ABSTRACT

A topical composition having improved healing properties, and particularly a lip balm for healing chapped, cracked, sunburned and windburned lips, and comprising up to 35 wt % aloe vera; 3 wt % or more salt; and a pharmaceutically acceptable topical medium.

2 Claims, No Drawings

LIP BALM COMPOSITION

FIELD OF THE INVENTION

The present invention concerns a topical composition having improved healing properties, and particularly a lip balm for healing chapped, cracked, sunburned and windburned lips.

DESCRIPTION OF THE RELATED ART

Lip balms have long been used to protect lips from the effects of the environment, such as sunlight, wind, and cold. Lip balms may be comprised of a variety of ingredients such as fats, oils, waxes and emollients which soften lips and protect against the effects of wind; agents which block damaging radiation from the sun; an other ingredients for imparting color, fragrance, and physical characteristics. See, e.g., U.S. Pat. No. 4,793,991 (Slimak).

Recently, it has become popular to incorporate aloe, or aloe vera, into commercial lip balms, ointments and lotions. Aloe vera has been used for over 2,000 years for a number of remedial applications, including topical application for treatment of sunburn, hemorrhoids, itching, blistering, skin blemishes, jellyfish bites, etc. Aloe vera is known to have anti-bacterial properties, as disclosed by Lorenzetti, et. al., J. Pharm. Sci. 53, 1287 (1964).

Aloe vera is a plant material derived from the leaves of one or more species of aloe. A list of species of aloe which have therapeutic value can be found in U.S. Pat. No. 4,646,029 (Grollier et al), the entire text of which is incorporated herein by reference.

Formulations of aloe for topical administration include those disclosed in U.S. Pat. No. 4,725,438 (Leazer) which teaches an aloe ointment for treatment of minor burns comprising a base which may be a mixture of petrolatum, mineral oil, wool wax alcohol and mineral wax. U.S. Pat. No. 4,593,046 (Gruber) teaches a dermatological composition of which the primary ingredients are benzoyl peroxide and aloe vera, the aloe vera helping to reduce the undesirable reactions which would otherwise occur as a result of the benzoyl peroxide.

U.S. Pat. No. 4,646,029 (Grollier et al) discloses the usefulness of aloe extracts in a cosmetic composition for prevention of sun burn in view of an ability to absorb solar radiation in the UV range. Species of aloe are listed in column 2. U.S. Pat. 4,481,185 (Crollier et al) mentions the anti-sunburn properties of aloes juices in column 4.

U.S. Pat. No. 4,788,007 (Baron) teaches UV absorption properties of aloe, and teaches the use of aloe gel as liquid sunglasses applied topically in the eyes. U.S. Pat. No. 4,857,328 (Trenzeluk) teaches an anti-burn mixture containing aloe, petroleum (Example 1) and cetyl alcohol (Example 3).

U.S. Pat. No. 3,892,853 teaches a process for preparing stabilized aloe gel, and U.S. Pat. No. 4,179,372 (Coats) teaches a process for stabilizing aloe vera gel comprising oxidizing the gel under heat, and adding ascorbic and citric acids. U.S. Pat. No. 5,118,673 (Carpenter et al) provides an extensive discussion of the history, biological properties, and pharmacy of aloe products, the entire text of which is incorporated herein by reference. Carpenter et al discuss rapid healing of radiation burns with aloe vera gel in column 7, line 39.

The composition and manner of action of aloe vera is not fully understood. It has been reported that steroids and wound healing hormones may be contained in aloe vera, but it is more commonly believed that the moisturizing emollient and healing properties of aloe vera are due to the polysaccharides present, or to synergistic effects of the polysaccharides and other substances present in the gel. Leun, A.; Effective Ingredients of Aloe Vera, Drugs & Cosmetics, June 1977, pp. 34–5 and 154–5.

Despite the incorporation of aloe into lip balms, people working outdoors do not find the commercially available compositions capable of providing relief from chapping, cracking, sunburning, and windburning of the lips. There remains a need for a topical composition capable of speeding the healing of such lips.

SUMMARY OF THE INVENTION

An object of the invention is to provide a dermatological composition having improved topical therapeutic properties.

A further object of the invention is to provide a lip balm composition able to more rapidly heal chapped, cracked, sunburned and windburned lips.

A further object of the invention is to provide a lip balm composition which remains on the lips longer than a conventional lip balm composition.

The achievement of the above and other objects of the invention has been accomplished on the basis of the discovery of the surprising effect which occurs when common table salt is added to a vehicle, such as a conventional lip balm composition, and this modified vehicle is applied to the skin or, preferably, to lips, and particularly chapped, cracked, or wind- or sun-burned lips. The lip balm according to the invention has even been found to accelerate the healing of cold sores. Accordingly, the healing properties of the lip balm of the present invention is greatly improved over the commercially available lip balms.

In addition to healing properties, the composition, when used as a lip balm, also feels good, and makes lips feel smoother and moister. While conventional lip balm compositions have been found to "wear off" after approximately fifteen minutes, requiring reapplication, the lip balm of the present invention remains on the lips for several hours, leaving the lips feeling softer longer.

The lip balm is preferably one which contains aloe as an active ingredient. In this case, the aloe and the salt are considered to be the main active ingredients, and any cosmetic vehicle which does not adversely effect the efficacy and stability can be used as the vehicle for these active ingredients.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other topical compositions for carrying out the same purposes of the present invention. It should also be realized by those skilled in the art that such equivalent compositions do not depart from the spirit and scope of the invention as set forth in the appended claims.

DETAILED DESCRIPTION OF THE INVENTION

The topical cosmetic composition according to the present invention can take any form for topical administration, but is particularly suited for use as a lip balm, and may be in the form of a stick, salve, cream, or ointment.

The three main ingredients are (1) salt, (2) aloe and (3) the cosmetic vehicle.

The salt may be any non-toxic, pharmaceutically acceptable salt, but is preferably an inorganic salt, most preferably a commercially available form of sodium chloride, such as table salt, iodized salt, sea salt, rock salt, etc. Other forms of salt such as sodium iodide or sodium bromide may be used, but for economic reasons of cost and availability, sodium chloride is preferred.

The amount of salt may be varied depending upon the carrier composition, but the salt is preferably present in an amount of at least 3 wt %, more preferably at least 5 wt %. Above 40 wt % there is no real gain in healing properties of the salt, and thus the salt is preferably present in an amount of from 3 to 40 wt %, more preferably from 5 to 30 wt %, most preferably about 20 wt %, depending upon the carrier.

The term "aloe" as used herein generally refers to the viscous gel of the internal portion of the leaf of plants of the genus aloe, and preferably of the species Aloe vera (e.g., Aloe vera Linne), *Aloe barbadensis* Miller, known in commerce as Curacao Aloe, or of *Aloe ferox* Miller and hybrids of this species with *Aloe africana* Miller and *Aloe spicata* Baker, known in commerce as Cape Aloe (Fam. Liliaceae). The gel may be in the form of a liquid concentrate from which water has been removed from gel which has been freshly extracted from the leaf of Aloe vera and to which preservatives have been added to preserve the therapeutic qualities of the gel.

A suitable aloe vera gel (concentrate) is commercially available from Terry Laboratories, Inc., 390 Wickham Road North, Melbourne, FL 32934. The inner gel (fillet) of freshly harvested leaves of the *Aloe Vera Barbadensis* Miller variety is carefully removed to minimize disruption of the Aloin layer (aloin being a thick, mucilaginous yellow juice, which is to be distinguished from the clear gel of aloe vera which is preferably employed in the present invention). The gel is next further processed to remove pulp and fiber. The resultant gel is then pasteurized and preserved to maintain its efficacy. Finally, the gel is concentrated utilizing low temperature evaporation to produce concentrates, and "decolorized" to remove color bodies and reduce the odor to ensure color stability and minimize the aloe's inherent pungency.

Products of Terry Laboratories suitable for use in the present invention include "Aloe Vera Decolorized 10×" (i.e., ten-times concentrate), a water-soluble colorless liquid with a slight vegetable odor, a boiling point of 100° C., and a specific gravity at 25° C. of 1.02, and "Aloe Vera Decolorized 40×" (i.e., 40 times concentrate), a water-soluble yellow to amber liquid with a moderate vegetable odor, a boiling point of 100° C., and a specific gravity at 25° C. of 1.11. Further details of the product are discussed in U.S. Pat. No. 4,593,046 (Gruber), the text of which is incorporated herein by reference.

Other aloe types which have been tested and found satisfactory for purposes of the present invention include:

AG014—1 part concentrate to 9 parts water (10× concentrate)

AG045—1 part concentrate to 39 parts water (40× concentrate)

AG006—aloe vera gel thickened—cosmetic grade C.T.F.A. Aloe Vera Gel and Carbomer 940 (98% aloe)

Other forms of aloe which may be used include an extract from the dried leaves of Aloe Vera plant as described in U.S. Pat. No. 4,857,328 (Trenzeluk). Trenzeluk teaches a skin therapeutic mixture comprising the Aloe Vera plant extract, a preservative such as a sulfathiazole, an oil such as stearic acid or cetyl alcohol or glycerol monostearate, and an oil-soluble base such as petrolatum.

The aloe vera may be omitted or used in any amount, preferably 5 to 35 wt %, most preferably in an amount which would correspond to 10 to 20 wt % of reconstituted aloe vera. That is, the addition of 0.25% of 40× concentrate would correspond to addition of 10 wt % of reconstituted (unconcentrated) aloe vera gel.

Preferably, aloe vera and salt are provided in approximately equal measure, or with a slightly greater wt % of salt.

The vehicle may be any cosmetic vehicle which, in the case that aloe vera is used, does not react with aloe vera, and is otherwise toxicologically and pharmaceutically acceptable. Preferred examples include petrolatum, a mineral oil (vaseline oil), which may be any petroleum based product; modified or unmodified vegetable oils such as peanut oil, wheatgerm oil, linseed oil, jojoba oil, apricot kernel oil, walnut oil, palm oil, pistachio oil, sesame oil, colza oil, cade oil, corn germ oil, peach kernel oil, poppyseed oil, pine oil, castor oil, soya oil, safflower oil, coconut oil, hazelnut oil, grapeseed oil, avocado oil, soy oil, sweet almond oil, calophyllum oil, castor oil, olive oil, sunflower oil, or animal oils such as whale oil, seal oil, menhaden oil, halibut liver oil, cod liver oil, cod, tuna, turtle tallow, horse's hoof, sheep's foot, mink, otter, marmot oil and the like; synthetic oils such as silicon oil such as dimethylpolysiloxane; alkyl and alkenyl esters of fatty acids, such as isopropyl esters of myristic, palmitic and stearic acids and fatty esters which are solid at room temperature; waxes such as lanolin wax, candelilla wax, spermaceti, cocoa butter, karite butter, silicon waxes, hydrogenated oils which are solid at room temperature, sucro-glycerides, oleates, myristates, linoleates, stearates, paraffin, beeswax, carnauba wax, ozokerite, candelilla wax, microcrystalline wax; fatty alcohols such as lauryl, cetyl, myristyl, stearyl, palmityl and oleyl alcohols; polyoxyethylated fatty alcohols; and wax esters, lanolin and its derivatives, perhydrosqualene and saturated esters, ethyl palmitate, isopropyl palmitate, alkyl myristates such as isopropyl myristate, butyl myristate and decyl myristate, hexyl stearate, triglyceride esters, triglycerides of octanoic and decanoic acid, cetyl ricinoleate, stearyl octanoate (Purcellin oil), fatty acids, polyhydric alcohols, polyether derivatives, fatty acid monoglycerides, polyethylene gylcol, propylene glycol, alkyl ethoxy ether sulfonates, ammonium alkyl sulfates, fatty acid soaps, and hydrogenated polyisobutene, and mixtures of waxes and oils.

The lip balm compositions according to the present invention can also contain the various ingredients usually contained in cosmetic or lip balm compositions, such as dyestuffs, pigments, perfumes, and preservatives. It is possible also to include additives which increase protection against sunburn, such as UV absorbers, coffee oil, derivatives of salicylic acid, derivatives of cinnamic acid, derivatives of para-aminobenzoic acid, derivatives of benzophenone and derivatives of camphor. Further optional additional ingredients include chelating agents such as gluconic, citric and tartaric acids, thickening agents such as cross-linked carboxyl polymethylene polymers, bentonite and gums, emulsifiers, fragrance materials, water, alcohol or acetone as necessary to achieve the desired cosmetic characteristics.

The pH of these compositions is preferably 5 to 7. Citric acid may be used to adjust pH as necessary.

The topical cosmetic composition according to the invention can be made on a small scale by mixing table salt and optionally aloe with a conventional commercially available lip balm, preferably an aloe-containing lip balm composition, in the following manner.

EXAMPLE 1

In a small sauce pan, 1⅛ tablespoon aloe and 1⅛ tablespoon salt were mixed and simmered at a temperature of 75° to 82° C. until the salt has completely dissolved, which takes about 5 minutes. Then, 0.15 oz. (4.2 grams) of the commercially available "Chap-Stick" are added in and the composition is simmered until all ingredients are thoroughly mixed. The composition is not brought to a boil. The composition is then allowed to cool to form a semi-solid at room temperature.

EXAMPLE 2

The following ingredients, in the following amounts, are mixed in a sauce pan in the same manner as set forth in Example 1:

(1) table salt (20 wt %)
(2) aloe (20 wt %)
(3) chap stick (60 wt %)—(comprising petrolatums (44%), lanolin (0.1%), cetyl alcohol (0.5%), padimate (1.5%), isopropyl myristate (1%), cetyl alcohol (0.5%), padimate (1.5%), isopropyl myristate (1%), balance inert)

Blending may be accomplished by intensive milling rather than heating, but in the absence of milling equipment, heating is preferred.

EXAMPLE 3

The same procedure as in Example 2 is repeated, with the following ingredients:

1. 20 wt % Aloe vera gel—type AG006 20 wt % table salt balance vaseline
2. 20 wt % Aloe vera gel—type AG006 20 wt % table salt balance "Chap-Stick"
3. 10 wt % Aloe vera gel—type AG006 10 wt % table salt balance vaseline
4. 10 wt % Aloe vera gel—type AG006 10 wt % table salt balance "Chap-Stick"
5. 20 wt % Aloe vera gel—type AG014 20 wt % table salt balance vaseline
6. 20 wt % Aloe vera gel—type AG014 20 wt % table salt balance "Chap-Stick"
7. 20 wt % Aloe vera gel—type AG045 20 wt % table salt balance vaseline
8. 20 wt % Aloe vera gel—type AG045 20 wt % table salt balance "Chap-Stick"

EXAMPLE 4

In a small sauce pan, 1⅛ tablespoon salt and 1½ cup water are mixed and brought to a boil for over a period of 7 minutes. The solution is allowed to cool to room temperature. Excess salt precipitates. The aqueous phase containing fully dissolved salt is poured off into a second sauce pan and into the solution is mixed 1⅛ tablespoon aloe. This mixture is simmered at a temperature of 75° to 82° C. for about 5 minutes. Then, 0.15 oz. (4.2 grams) of the commercially available "Chap-Stick" is added in and the composition is simmered until all ingredients are thoroughly mixed. The composition is not brought to a boil. The composition is then allowed to cool to form a semi-solid at room temperature.

The compositions produced in accordance with Examples 1, 2, 3 and 4 were applied topically to healthy lips as a preventative prior to prolonged work outdoors in sun and wind. The lip balm remained on the lips for several hours, and the lips remained moist and free of cracks or sun or wind burns. The lip balm of Example 4, wherein the salt was first dissolved in water, felt smoother on the lips than the lip balm of Example 1.

The compositions were applied to cracked lips, including lips with aggravated slits and sores in the corners of the mouth. After a single day, the lips were healed and restored to normal, despite the fact that conventional lip balms and antiseptics had not been able to bring about a cure.

The surprising results observed when salt is added to a lip balm or topical composition is not understood. Healing mechanisms associated with known methods of using salt do not correlate with or explain the present invention. For example, there is a well known folk remedy for a sore throat which comprises gargling with salt water. However, the mechanism of action resides in washing away of mucus and the associated bad breath, reducing swelling of tissues, and mild antiseptic properties, which can not be correlated with the application of salt to the skin for several hours in accordance with the present invention for promotion of tissue healing.

It is also known to irrigate the nostril passages with isotonic saline. However, there is no correlation between, on the one hand, these "rinses" and on the other hand, the application of salt to the lips in the form of a balm to promote healing.

It is also known that salt can be used as a preservative for fish or meat. However, the salinity of a lip balm can not be compared to the salt applied in the salting of fish or meat. The small amount of salt in a lip balm would not have a sufficient concentration to act as a preservative in the known manner, and the characteristics of a lip balm composition are clearly quite different from pure salt. Further, the lip balm of the present invention is characterized by the promotion of rapid healing, which is a different phenomenon from long term preservation.

Finally, it is said to be extremely painful to rub salt in a wound. This would indicate that salt should not be applied to cracked lips, which are an area of high sensitivity, or any open wound, cut or sore on any area of the body. In view of the above, there would appear to be no logical reason for the incorporation of salt into a composition for topical administration. It is quite surprising that the composition of the present invention can be used to promote healing of, for example, a papercut on a finger or the cracks in the corners of the mouth, and that lips are not adversely effected. In fact, lips remain moist and free of burns and cracks despite working outdoors in sun and wind.

Although the topical composition first designed for protecting and promoting healing of lips, and thus is particularly suited for use as a lip balm, the special properties of the topical composition the it suitable for use in a number of other cosmetic and medical applications. Although this invention has been described in its preferred form with a certain degree of particularity with respect to a lip balm composition, it is understood that the present disclosure of the preferred form has been made only by way of example and that numerous changes in the details of structures and the composition of the topical composition may be resorted to without departing from the spirit and scope of the invention.

Now that the invention has been described,

What is claimed is:

1. A method for restoring chapped or burned lips, comprising topically administering to such lips a mixture comprising:

up to 35 wt % aloe vera gel;

from 3 wt % or more salt; and a pharmaceutically acceptable medium.

2. A method for manufacturing a topical composition for protection of lips and alleviating chapped or burned lips, comprising the steps of:

mixing an excess of salt into water;

heating the mixture to dissolve the salt;

cooling the mixture until excess salt precipitates;

pouring off the supernatant and mixing the supernatant with aloe with heat;

mixing a topical carrier composition into the thus heated mixture with heat; and cooling to form a solid or semi-solid comprising up to 35 wt % of aloe and 3wt % or more salt.

* * * * *